United States Patent
Kim et al.

(10) Patent No.: US 7,309,788 B2
(45) Date of Patent: Dec. 18, 2007

(54) METHOD FOR PREPARING PYRIMIDINONE COMPOUND AND PHARMACEUTICALLY ACCEPTABLE SALTS THEREOF

(75) Inventors: Sang-Lin Kim, Seoul (KR); Ji-Han Kim, Seoul (KR); Jung-Bok Lee, Gyunggi-do (KR); Byoung-Wug Yoo, Gyunggi-do (KR); Hyun-Kwang Tan, Seoul (KR)

(73) Assignee: Boryung Pharmaceutical Co., Ltd., Seoul (KR)

( * ) Notice: Subject to any disclaimer, the term of this patent is extended or adjusted under 35 U.S.C. 154(b) by 521 days.

(21) Appl. No.: 10/490,294

(22) PCT Filed: Sep. 21, 2001

(86) PCT No.: PCT/KR01/01583

§ 371 (c)(1),
(2), (4) Date: Aug. 25, 2004

(87) PCT Pub. No.: WO03/024956

PCT Pub. Date: Mar. 27, 2003

(65) Prior Publication Data

US 2004/0266800 A1   Dec. 30, 2004

(51) Int. Cl.
*C07D 401/10* (2006.01)
(52) U.S. Cl. .................................... 544/319
(58) Field of Classification Search ................ 544/319
See application file for complete search history.

(56) References Cited

U.S. PATENT DOCUMENTS 5,869,476 A   2/1999   Paik et al.
6,294,542 B1   9/2001   Lee et al.

*Primary Examiner*—Deepak Rao
(74) *Attorney, Agent, or Firm*—Fish & Richardson P.C.

(57) ABSTRACT

A process for preparing pyrimidinone compound and salts thereof The method of the present invention enables the convenience to produce the pyrimidinone derivatives in high yields, which pyrimidinone compounds are useful for treating cardiovascular diseases caused by binding angiotensin II to its receptors, through antagonistic activity against angiotensin II receptors.

20 Claims, No Drawings

METHOD FOR PREPARING PYRIMIDINONE COMPOUND AND PHARMACEUTICALLY ACCEPTABLE SALTS THEREOF

This application is a 371 of PCT/KR01/01583 filed Sep. 21, 2001.

TECHNICAL FIELD

The present invention relates to a process for preparing pyrimidinone compound and pharmaceutically acceptable salts thereof. More particularly, the present invention relates to a convenient and high productive process for producing pyrimidinone compound of the following Formula 1 and its pharmaceutically acceptable salts, which compounds are useful for treating cardiovascular diseases caused by binding angiotensin II to its receptors, through antagonistic activity against angiotensin II receptors.

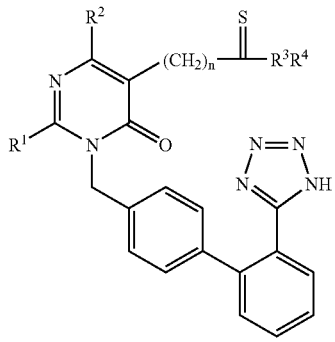

Formula 1 wherein, $R^1$ is $C_1$-$C_4$ straight or side chain alkyl, cycloalkyl, $C_1$-$C_4$ alkylalkoxy or $C_1$-$C_4$ alkylmercapto;

$R^2$ is H, halogen, $C_1$-$C_4$ straight or side chain alkyl or arylalkyl;

$R^3$, $R^4$ which are the same or different from each other, represent H, $C_1$-$C_4$ straight or side chain alkyl, cycloalkyl, carbocyclic aryl, arylalkyl, arylcarbonyl, $C_1$-$C_4$ alkoxycarbonyl, or aminocarbonyl, being optionally substituted by H, halogen, hydroxy, $C_1$-$C_4$ alkoxy, amino, alkylamino or dialkylamino (each alkyl residue having $C_1$-$C_5$), $C_1$-$C_4$ alkoxycarbonyl or carboxy, $R^3$ and $R^4$ are together with N atom forming 4 to 8 membered heterocyclic ring which can be further substituted with one or two substituents selected from the group consisting of cycloalkyl, carbocyclic aryl or arylalkyl, halogen, hydroxy, $C_1$-$C_4$ alkoxy, amino, alkylamino or dialkylamino (each alkyl residue having $C_1C_5$), $C_1$-$C_4$ alkoxycarbonyl, carboxy or aminocarbonyl, and $C_1$-$C_4$ straight or side chain alkyl, wherein said heterocyclic ring can further include —O—, —S—, —SO—, —SO$_2$— or >N—$R^5$; $R^5$ is H, $C_1$-$C_4$ alkyl, carbocyclic aryl, arylalkyl, substituted alkenyl, pyridyl, pyrimidyl, $C_1$-$C_4$ alkyl or arylcarbonyl, $C_1$-$C_4$ alkoxy carbonyl, aminocarbonyl, CN or SO$_2$NR$^3$R$^4$;

n is an integer selected from 1, 2, 3, 4, 5 and 6.

BAKGROUND ART

Recently, numerous researches have been conducted on non-peptide angiotensin II antagonist (U.S. Pat. Nos. 4,207,324; 4,340,598; 4,576,958; 4,582,847 and 4,880,804; European Laid-Open Patent Publication Nos. 028,834; 245,637; 253,310; 291,969; 323,841 and 324,377, etc.) Among the above, EP Laid-Open Patent Publication Nos. 028,834 and 253,310 disclose imidazole derivatives substituted with biphenyl group (eg. Losartan) and EP Laid-Open Patent Publication No. 245,637 disclose imidazolepyridine derivatives (eg. L158,809). These compounds are asserted to have strong angiotensin II antagonistic effect. Besides, EP Laid-Open Patent Publication Nos. 407,342, 419,048 and 445,811 disclose pyrimidinone compound, that is, a 6 membered heterocyclic compound containing an additional nitrogen atom compared to a 5 membered imidazole derivative mentioned above. However, those pyrimidinone compounds exert less activity than imidazole derivatives.

As a result of intensive study on pyrimidinone compounds, the present inventors had developed a novel pyrimidinone compound having basically different structure compared to the above pyrimidinone compounds, while having significantly superior activity, that is, as high as 50 times more than that of the aforementioned imidazole derivatives [in vitro (rabbit aorta) inhibition rate of 60-70% at $10^{-8}$~$10^{-9}$ mole conc.] and filed patent applications therefor (International Application Nos. PCT/KR95/00121, filed Sep. 15, 1995; and PCT/KR 9900198, filed Apr. 26, 1999). The developed pyrimidinone compounds of Formula 1 have been produced as depicted in the following Reaction Scheme 1, as disclosed in both of the above applications.

Reaction Scheme 1

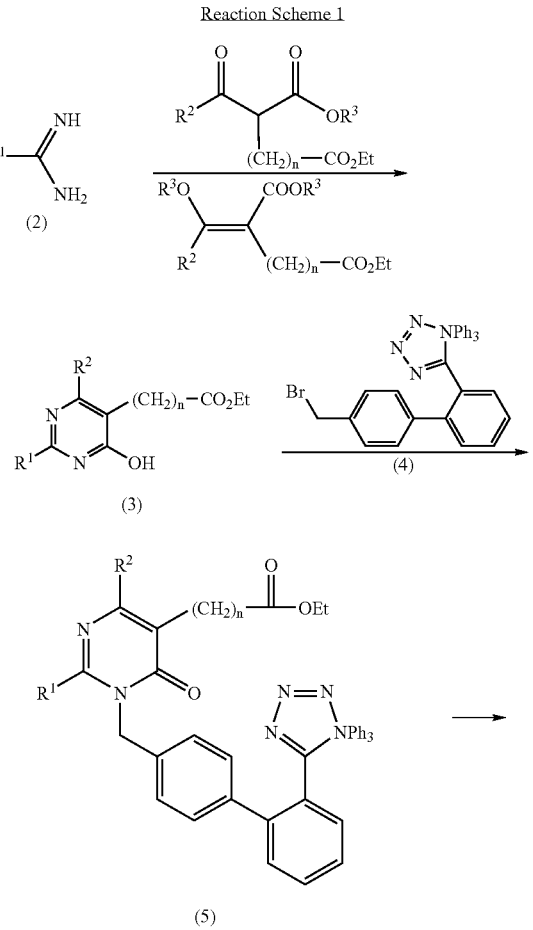

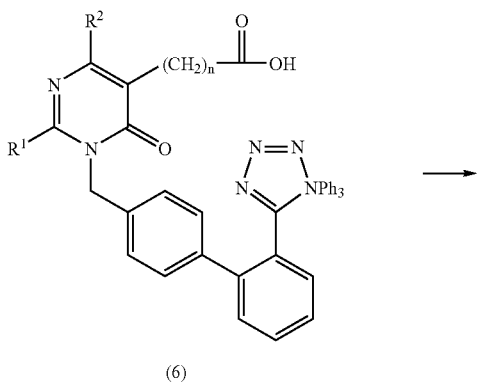

(6)

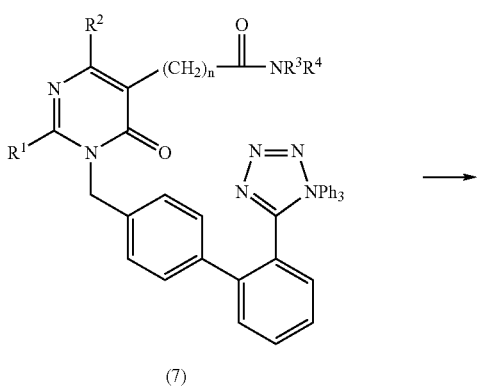

(7)

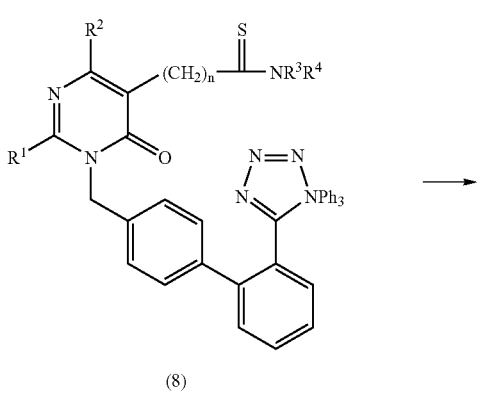

(8)

wherein, $R^1$, $R^2$, $R^3$, $R^4$, $R^5$ and n are as defined in the above.

However, the aforementioned process comprising multiple steps is somewhat very complicated, and it is also very difficult to isolate the compound of Formula 5 due to the non-selective reactions of N, O-alkylated compounds, which inevitably entail an inconvenience involved with column purification and a disadvantage of very poor yield (1.28%).

SUMMARY OF THE INVENTION

The present invention solves the aforementioned prior art problems by providing a novel process for preparing a pyrimidinone compound of Formula 1, in which the process comprises the steps of: inducing a selective N-alkylation reaction by adding a base to the compounds of Formula 3 and Formula 4 in an organic solvent mixture so as to obtain the above compound of Formul 5; hydrolysing and amidating the compound of Formula 5 simultaneously to obtain the compound of Formula 7; conducting a thioamidation reaction of the compound of Formula 7 by using Lawessons's reagent without acid treatment; and treating the obtained product with alcoholic reagent.

Therefore, it is an object of the present invention to provide a process for producing a pyrimidinone compound and salts thereof in a relatively simple and high productive manner.

Further, it is other object of the present invention to provide hydrates of the pyrimidinone compound produced by the above process and pharmaceutically acceptable salts thereof.

Any other objects of the present invention will be clearly understood in view of the following detailed description.

DISCLOSURE OF INVENTION

The present invention relates to a preparation process of the compounds of Formula 1 and their salts as illustrated in the following Reaction Scheme 2, comprising the steps of thioamidating the compound of Formula 7 by using Lawessons's reagent and then treating the product with alcoholic reagent.

Reaction Scheme 2

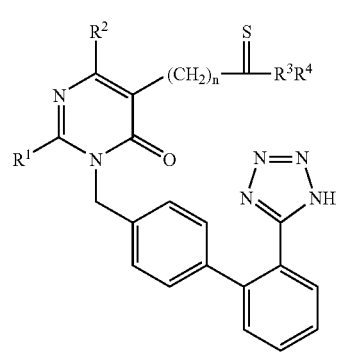

(1)

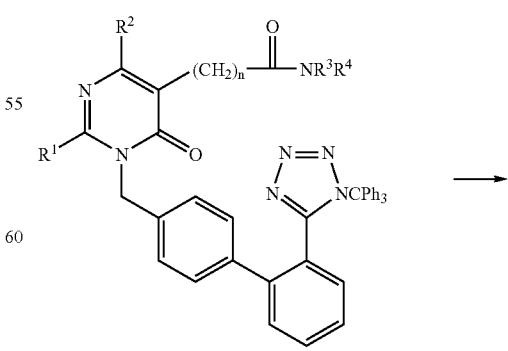

(7)

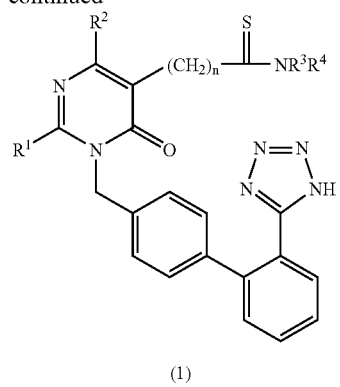

(1)

wherein,

R[1] is $C_1$-$C_4$ straight or side chain alkyl, cycloalkyl, $C_1$-$C_4$ alkylalkoxy or $C_1$-$C_4$ alkylmercapto;

R[2] is H, halogen, $C_1$-$C_4$ straight or side chain alkyl or arylalkyl

R[3], R[4] which are the same or different from each other, represent H, $C_1$-$C_4$ straight or side chain alkyl, cycloalkyl, carbocyclic aryl, arylalkyl, arylcarbonyl, $C_1$-$C_4$ alkoxycarbonyl, or aminocarbonyl, being optionally substituted by H, halogen, hydroxy, $C_1$-$C_4$ alkoxy, amino, alkylamino or dialkylamino (each alkyl residue having $C_1$-$C_5$), $C_1$-$C_4$ alkoxycarbonyl or carboxy, R[3] and R[4] are together with N atom forming 4 to 8 membered heterocyclic ring which can be further substituted with one or two substituents selected from the group consisting of cycloalkyl, carbocyclic aryl or arylalkyl, halogen, hydroxy, $C_1$-$C_4$ alkoxy, amino, alkylamino or dialkylamino (each alkyl residue having $C_1$-$C_5$), $C_1$-$C_4$ alkoxycarbonyl, carboxy or aminocarbonyl, and $C_1$-$C_4$ straight or side chain alkyl, wherein said heterocyclic ring can further include —O—, —S—, —SO—, —SO$_2$— or >N—R[5]; R[5] is H, $C_1$-$C_4$ alkyl, carbocyclic aryl, arylalkyl, substituted alkenyl, pyridyl, pyrimidyl, $C_1$-$C_4$ alkyl or arylcarbonyl, $C_1$-$C_4$ alkoxy carbonyl, aminocarbonyl, CN or $SO_2NR^3R^4$;

n is an integer selected from 1, 2, 3, 4, 5 and 6.

Hereinafter, the preparation process according to the present invention is explained in more detail.

The present invention provides a process for producing a pyrimidinone compound of Formula 1 and salts thereof, comprising the steps of thioamidating the compound of Formula 7 by using Lawessons's reagent and then treating the product by alcoholic reagent. According to the present process, a pyrimidinone compound of Formula 1 can be conveniently obtained in a single step with high yield by conducting thioamidation reaction. The pharmaceutically acceptable salts thereof are produced by adding a salt to the obtained pyrimidinone compound pursuant to the conventional methods. The Lawessons's reagent is used in an amount of 0.5~2.0 eq, preferably in the amount of 1.0 eq during thioamidation. Then, the protecting groups are treated with alcoholic reagent, preferably selected from methanol, ethanol, propanol and mixtures thereof. As a salt, potassium salt or sodium salt is preferably used.

The compound of Formula 7 is prepared by simultaneously conducting hydrolysis and amidation of the compound of Formula 5 simultaneously, as outlined in the following Reaction Scheme 3, wherein hydrolysis is conducted by using sodium hydroxide, and amidation is conducted by using amine and N-hydroxybenzotriazole, N-methylmorpholine and dicyclohexylcarbodiimide in an amount of 1 eq. in chloroform.

Reaction Scheme 3

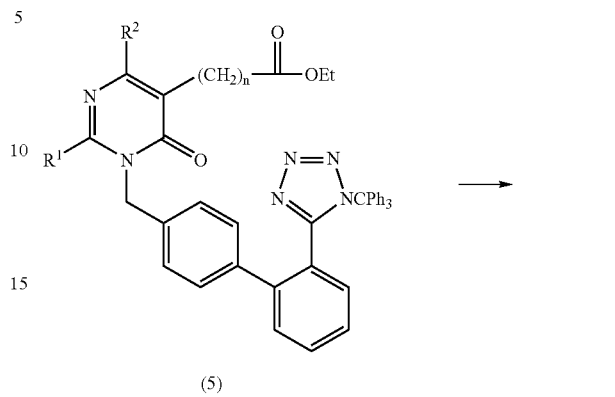

(5)

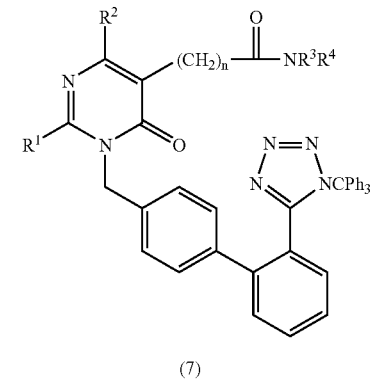

(7)

The compound of Formula 5 can be easily obtained by selectively forming N-alkylated compound by adding a base into the compounds of Formulae 3 and 4 in a mixed organic solvent Reaction Scheme 4

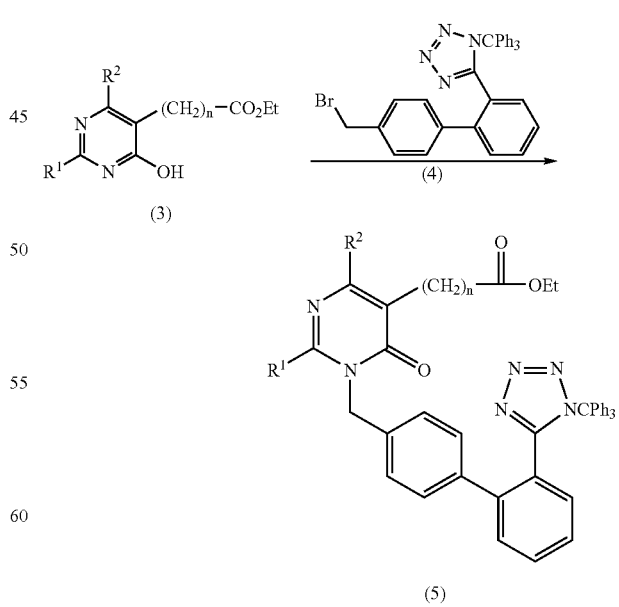

(5)

As a mixed organic solvent, a mixture of dimethylformamide and ethylacetate is used, preferably in a mixing ratio of 1~50 : 50~1, and more preferably 1~10 : 10~1. Further, as a base, it can be mentioned alkali metal hydrides or organic salts of alkali metal, and it is most preferred to use lithium hydride among the alkali metal hydrides.

Consequently, according to the process of the present invention, it is possible to prepare N-alkylated compound of Formula 5 in a high selectivity, which further enables a convenient operation in separation and purification steps. Further, it is possible to produce pyrimidinone compound of Formula 1 in a remarkably high yield (28.2%).

The present invention also provides hydrates of the pyrimidinone compound produced by the aforementioned process and pharmaceutically acceptable salts thereof. As described above, the pyrimidinone compound of Formula 1 is disclosed in the International Application Nos. PCT/KR95/00121, filed Sep. 15, 1995 and PCT/KR9900198, filed Apr. 26, 1999. However, in case the above compound exists in a state of anhydride, it has a tendency to absorb moisture from the air. Thus, if a medicine is produced with anhydrides of the above pyrimidinone compound, it becomes unstable because of moisture in the air.

The invention will be further illustrated by the following examples. It will be apparent to those having conventional knowledge in the field that these examples are given only to explain the present invention more clearly, but the invention is not limited to the examples given.

MODES FOR CARRYING OUT THE INVENTION

PREPARATION EXAMPLE 1

Preparation of 2-n-butyl-5-ethoxycarbonylmethyl-4-hydroxy-6-methyl-pyrimidine 1.41 kg of valeroamidine and 1.41 kg of diethyl acetylsuccinate were dissolved in 4.5 L of methanol and 1.16 kg of potassium hydroxide was added thereto. The mixture was stirred for 15 hours at room temperature, and then 14 L of water was added while stirring. The obtained solid was filtered, dried, and dissolved in 6 L of ethanol. Then, 840 g of thionyl chloride was added by drop for 2 hours and stirred for 12 hours at 60° C. To this mixture was added a solution of 1.22 kg of sodium bicarbonate in 15 L of water and the produced solid was filtered and dried to obtain 1.35 kg (47.8% yield) of the titled compound.

IR (KBr) cm$^{-1}$: 1740, 1665, 1620

$^1$H NMR (DMSO-d$_6$): δ 0.89(t, 3H), 1.1.2(t, 3H), 1.20~1.40(m, 2H), 1.52-1.70(m, 2H), 2.18(s, 3H), 2.50(t, 2H), 3.45(s, 2H), 4.08(q, 2H), 12.38(brs, 1H).

EXAMPLE 1

Preparation of 2-n-butyl-5-ethoxycarbonylmethyl-6-methyl-3-[[2'-(N-triphenylmethyltetrazol-5-yl)biphenyl-4-yl]methyl]-pyrimidin-4(3H)-one 1.35 kg of the compound of Preparation Example 1 was dissolved in 18 L of a mixed solution of dimethylformamide and ethylacetate (mixing ratio 1:8) and cooled to 0° C. To this, 47 g of lithium hydride was added and stirred for 30 minutes. Then 4.26 kg of 4-[2'-(N-triphenylmethyltetrazole-5-yl)phenyl]benzyl bromide was added to the obtained mixed solution and stirred for 90 hours at 55° C. The product was filtered and dried to obtain 3.54 kg (90% yield) of the selectively N-alkylated titled compound.

IR (neat) cm$^{-1}$: 1740, 1665, 1600.

$^1$H NMR (CDCl$_3$): δ 0.86(t, 3H), 1.25(t, 3H), 1.52~1.70 (m, 4H), 2.30(s, 3H), 2.52(t, 2H), 3.63(s, 2H), 4.18(q, 2H), 5.19(s, 2H), 6.85~6.98(m, 7H), 7.05~7.12(m, 3H), 7.20~7.40(m, 9H), 7.40~7.50(m, 3H), 7.90~7.95(dd, 1H).

EXAMPLE 2

Preparation of 2-n-butyl-5-dimethylaminocarbonylmethyl-6-methyl-3-[[2'-(N-triphenylmethyltetrazol-5-yl)biphenyl-4-yl]methyl]-pyrimidin-4(3H)-one 2.75 kg of the compound of Example 1 was dissolved in 8 L of a mixed solution of methanol and tetrahydrofuran (mixing ratio 1:3) and cooled to 0° C. To this, 2 L of 10% solution of sodium hydroxide was added for two hours and then stirred for 4 hours. 1.2 L of 4N hydrochloric acid was added to neutralize the solution and then vacuum concentrated to extract with 10 L of chloroform. Chloroform was concentrated to 6 L and thereafter, 330 g of dimethylamine hydrochloride, 550 g of N-hydroxybenzotriazole, 900 ml of N-methylmorpholine and 920 g of dicyclohexylcarbodiimide were sequentially added thereto at 0° C. and stirred for 15 hours at room temperature. The obtained solid was filtered and the filtrate was washed with 2 L of water and 2 L of saturated sodium bicarbonate, and vacuum concentrated. The residue was dissolved in 5 L of ethyl acetate and 10 L of hexane was added by drop to produce a solid product, which was further filtered and dried to obtain 1.97 kg (82%) of the titled compound.

IR (KBr) cm$^{-1}$: 1660, 1620,1555.

$^1$H NMR (CDCl$_3$): δ 0.87(t, 3H), 1.25~1.40(m, 2H), 1.55~1.75(m, 2H), 2.20(s, 3H), 2.58(t, 2H), 2.87(s, 3H), 3.11(s, 3H), 3.56(s, 2H), 5.10(s, 2H), 6.85~6.98(m, 8H), 7.11(dd, 2H), 7.22~7.38(m, 10H), 7.48(m, 2H), 7.98(dd, 1H).

EXAMPLE 3

Preparation of 2-n-butyl-5-dimethylaminothiocarbonylmethyl-6-methyl-3-[[2'-(1 H-tetrazol-5-yl)biphenyl-4-yl]methyl]-pyrimidin-4(3H)-one 1.97 kg of the compound of Example 2 was dissolved in 8 L of toluene and Lawesson's reagent (1.1 kg) was added thereto at room temperature. The turbid solution as obtained was reacted for 6 hours at 80° C. and cooled to the room temperature to filter out unnecessary solid material. Vacuum concentration was followed and 6 L of methanol was added to the residue and refluxed for 3 hours and concentrated. The obtained concentrate was dissolved in 4.5 L of ethyl acetate. 4.5 L of water was added thereto so as to produce solid product. The obtained solid product was filtered and washed with 1 L of water, 1 L of ethyl acetate and 3 L of isopropylether separately and dried for 24 hours at 60° C. to produce the 1.1 kg (80%) of the titled compound.

Melting point: 96.8~101.8° C.

TLC R$_f$: 0.28 (5% MeOH in CHCl$_3$)

$^1$H NMR (CDCl$_3$): δ0.89(t, 3H), 1.28~1.45(m, 2H), 1.58~1.74(m, 2H), 2.26(s, 3H), 2.63(t, 2H), 3.44(s, 3H), 3.46 (s, 3H), 3.77(s, 2H), 5.22(s, 2H), 7.07(s, 5H), 7.33~7.60 (m, 3H), 7.94(dd, 1H).

EXAMPLE 4

Stability of 2-n-butyl-5-dimethylaminothiocarbonyl-methyl-6-methyl-3-[[(2'-(1H-tetrazol-5-yl)biphenyl-4-yl]methyl]-pyrimidin-4(3H)-one

TABLE 1

| Time (hour) | Condition | | |
|---|---|---|---|
| | Room temperature & Room humidity | 60% RH | 75% RH |
| 1 | 3.4% | 6.2% | 9.05% |
| 2 | 5.6% | 9.1% | 9.1% |
| 3 | 9.1% | 9.15% | 9.1% |
| 4 | 9.2% | 9.1% | 9.15% |
| 5 | 9.1% | 9.2% | 9.2% |
| 6 | 9.1% | 9.1% | 9.1% |

As seen in the Table 1, the moisture content for the compound of Example 3 was hourly measured. As a result, the moisture content increased, as the time went by. However, after the fixed time went by, the content did not increased any more. From the result, we discovered that the hydrate of the pyrimidinone compound is more stable than the anhydride in the air. The elementary analysis data for the aforementioned hydrates is illustrated in the following Table 2.

TABLE 2

| | Content in theory (%) (molecular formula: $C_{27}H_{36}N_7OSK$) | Content in practice (%) |
|---|---|---|
| C | 54.61 | 54.82 ± 0.70 |
| H | 6.11 | 5.96 ± 0.20 |
| N | 16.51 | 17.47 ± 0.26 |
| O | 10.78 | 8.44 ± 0.14 |
| S | 5.40 | 5.46 ± 0.39 |

As it is verifiable in the above Table, the pyrimidinone compound absorbs the moisture, which turns into tri-hydrate type and is considered stable.

INDUSTRIAL APPLICABILITY

As described above, the present invention provides a process for producing a pyrimidinone compound of Formula 1 and salts thereof, comprising the steps of thioamidating a compound of Formula 7 by using Lawessons's reagent and then treating the product with alcoholic reagent. As exemplified in the aforementioned Example 1, the compound of Formula 5 can be produced by selectively processing N-alkylation reaction only, which in turn does not necessitate a purification process using a column in the entire process. Therefore, according to the present process, a pyrimidinone compound and its salts are obtained in much higher yield compared to the conventional process.

What is claimed is:

1. A process for preparing pyrimidinone compound of Formula 1 and pharmaceutically acceptable salts and hydrates thereof, comprising the steps of thioamidating a compound of Formula 7 by using Lawessons's reagent and then treating the product with alcoholic reagent, as illustrated in the following Reaction Scheme 2:

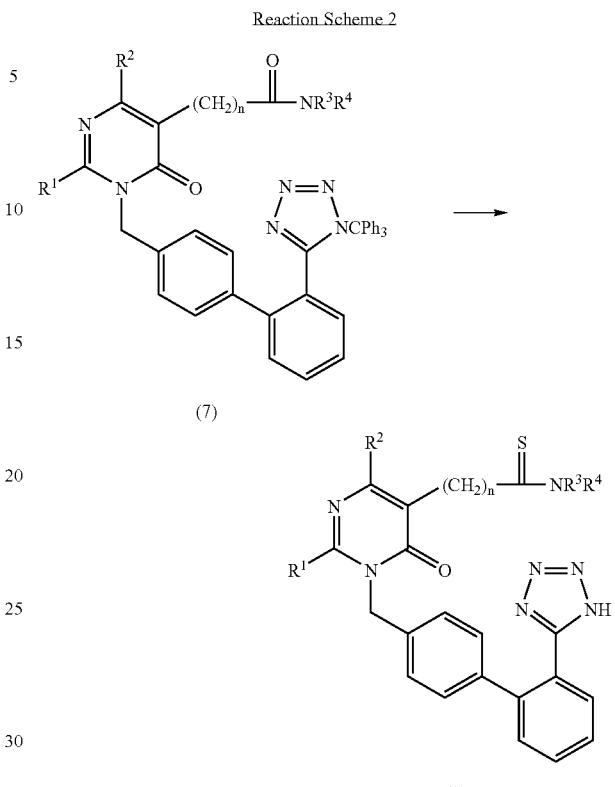

wherein, $R^1$ is $C_1$-$C_4$ straight or side chain alkyl, cycloalkyl, $C_1$-$C_4$ alkylalkoxy or $C_1$-$C_4$ alkylmercapto;

$R^2$ is H, halogen, $C_1$-$C_4$ straight or side chain alkyl or arylalkyl;

$R^3$ and $R^4$ which are the same or different from each other, represent H, $C_1$-$C_4$ straight or side chain alkyl, cycloalkyl, arylalkyl, or $C_1$-$C_4$ alkoxycarbonyl, being optionally substituted by H, halogen, hydroxy, $C_1$-$C_4$ alkoxy, amino, alkylamino or dialkylamino (each alkyl group having $C_1$-$C_5$), or $R^3$ and $R^4$ together with the nitrogen to which they are attached form a 4 to 8 membered heterocyclic ring which can be further substituted with one or two substituents selected from the group consisting of cycloalkyl, arylalkyl, halogen, hydroxy, $C_1$-$C_4$ alkoxy, amino, alkylamino dialkylamino (each alkyl group having $C_1$-$C_5$), and $C_1$-$C_4$ straight or side chain alkyl, wherein said heterocyclic ring can further include— O—, —S—, —SO—, —$SO_2$— or —N($R^5$)—;

$R^5$ is H, $C_1$-$C_4$ alkyl, carbocyclic aryl, arylalkyl, substituted alkenyl, pyridyl, pyrimidyl, or $C_1$-$C_4$ alkyl; and n is an integer selected from 1, 2, 3, 4, 5 and 6.

2. The process according to claim 1, wherein said Lawesson's reagent is used in an amount of 0.5-2.0 eq.

3. The process according to claim 1, wherein said alcoholic reagent is selected from the group consisting of methanol, ethanol, propanol, and mixtures thereof.

4. The process according to claim 1, wherein said compound of Formula 7 is obtained by conducting hydrolysis and amidation of the compound of Formula 5 simultaneously, as illustrated in the following Reaction Scheme 3:

Reaction Scheme 3

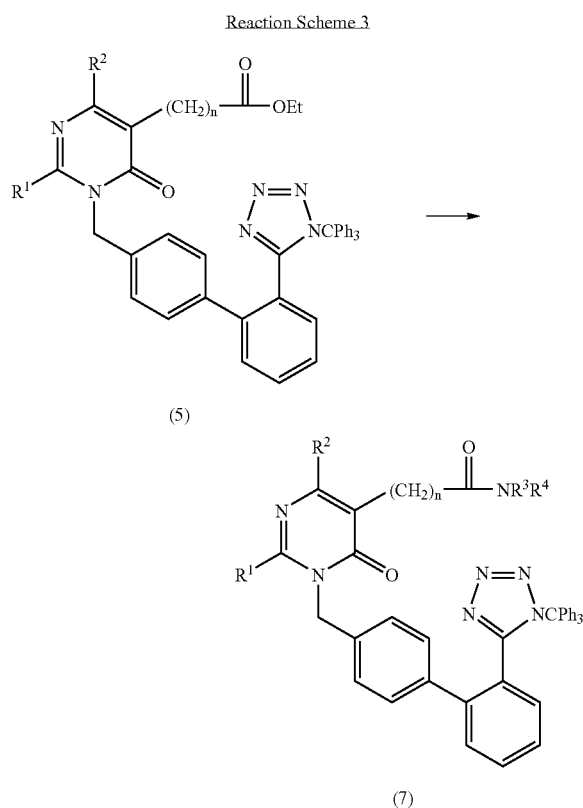

wherein, $R^1$, $R^2$, $R^3$, $R^4$, $R^5$ and n are as defined in claim 1.

5. The process according to claim 4, wherein the compound of Formula 5 is obtained by adding a base into the compound of Formula 3 and compound of Formula 4 in a mixed organic solvent, as illustrated in the following Reaction Scheme 4:

Reaction Scheme 4

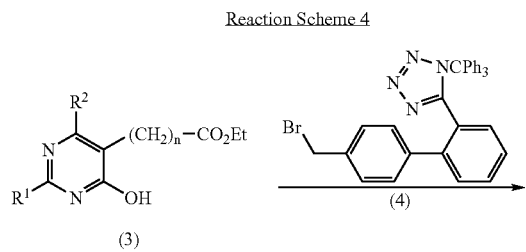

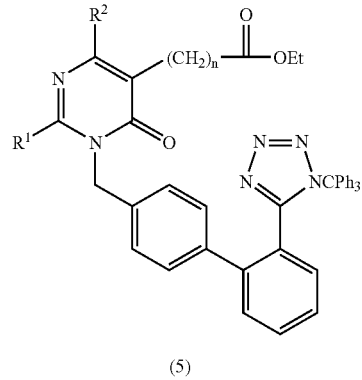

6. The process according to claim 5, wherein said mixed organic solvent is a mixed solvent of dimethylformamide and ethylacetate.

7. The process according to claim 5, wherein said base is an alkali metal hydride or an organic salt of an alkali metal.

8. The process according to claim 7, wherein said alkali metal hydride is lithium hydride.

9. The process according to claim 1, wherein said salt is sodium or potassium salt.

10. A tri-hydrate of a pyrimidinone compound or pharmaceutically acceptable salt thereof produced by the process of claim 1.

11. The process according to claim 2, wherein said salt is sodium or potassium salt.

12. The process according to claim 3, wherein said salt is sodium or potassium salt.

13. The process according to claim 4, wherein said salt is sodium or potassium salt.

14. The process according to claim 5, wherein said salt is sodium or potassium salt.

15. The process according to claim 6, wherein said salt is sodium or potassium salt.

16. The process according to claim 7, wherein said salt is sodium or potassium salt.

17. The process according to claim 8, wherein said salt is sodium or potassium salt.

18. The process according to claim 1, wherein said hydrate is a tri-hydrate.

19. The process according to claim 18, wherein said tri-hydrate is a hydrate of the sodium or potassium salt of a pyrimidinone compound of Formula 1.

20. The tri-hydrate according to claim 10, wherein said salt is the potassium or sodium salt.

* * * * *